United States Patent

Perronnet et al.

[11] 4,036,633
[45] July 19, 1977

[54] CROTONANILIDES

[75] Inventors: Jacques Perronnet; Pierre Girault, both of Paris, France

[73] Assignee: Roussel-UCLAF, Paris, France

[21] Appl. No.: 613,911

[22] Filed: Sept. 16, 1975

[30] Foreign Application Priority Data

Oct. 3, 1974  France .................. 74.33320

[51] Int. Cl.² .............. C07C 103/60; A01N 9/20; C07C 125/06
[52] U.S. Cl. .............. 71/106; 260/468 E; 260/479 R; 260/479 C; 260/562 A; 260/562 K
[58] Field of Search .............. 260/468 E, 479 C; 71/106

[56] References Cited

U.S. PATENT DOCUMENTS

| | | | |
|---|---|---|---|
| 3,792,994 | 2/1974 | Baker et al. | 260/479 C |
| 3,836,570 | 9/1974 | Szabo | 260/479 C |
| 3,857,693 | 12/1974 | Hill et al. | 260/479 C |
| 3,872,157 | 3/1975 | Brokke et al. | 260/479 C |

FOREIGN PATENT DOCUMENTS 2,348,487  4/1974  Germany

*Primary Examiner*—Lorraine A. Weinberger
*Assistant Examiner*—Michael Shippen

*Attorney, Agent, or Firm*—Hammond & Littell

[57] ABSTRACT

Novel crotonanilides of the formula

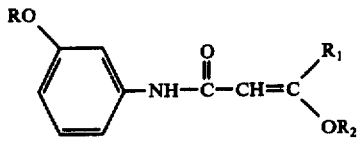

wherein R is selected from the group consisting of

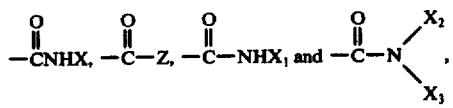

X is selected from the group consisting of alkyl of 1 to 8 carbon atoms and cycloalkyl of 3 to 7 carbon atoms, Z is alkyl of 1 to 6 carbon atoms, $X_1$ is alkoxyalkyl of 2 to 12 carbon atoms, $X_2$ is alkyl of 1 to 3 carbon atoms, $X_3$ is selected from the group consisting of alkyl or alkoxy of 1 to 3 carbon atoms and $R_1$ and $R_2$ are individually alkyl of 1 to 3 carbon atoms having pre- and post-emergence herbicidal activity.

23 Claims, No Drawings

CROTONANILIDES

OBJECTS OF THE INVENTION

It is an object of the invention to provide the novel crotonanilides of formula I' as well as a process for their preparation.

It is another object of the invention to provide novel herbicidal compositions and to provide novel pre- and/or post-emergence methods of killing weeds.

These and other objects and advantages of the invention will become obvious from the following detailed description.

THE INVENTION

The novel crotonanilides of the invention have the formula

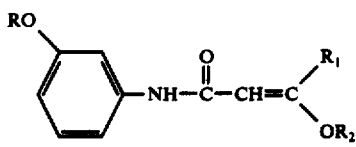

wherein R is selected from the group consisting of

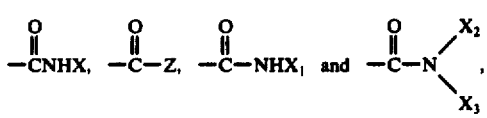

X is selected from the group consisting of alkyl of 1 to 8 carbon atoms and cycloalkyl of 3 to 7 carbon atoms, Z is alkyl of 1 to 6 carbon atoms, $X_1$ is alkoxyalkyl of 2 to 12 carbon atoms, $X_2$ is alkyl of 1 to 3 carbon atoms, $X_3$ is selected from the group consisting of alkyl and alkoxy of 1 to 3 carbon atoms.

In formula I', X is preferably methyl, ethyl, propyl, isopropyl and straight or branched chain butyl, pentyl or hexyl and cyclopropyl, cyclobutyl, cyclopentyl, cyclohexyl or cycloheptyl; $X_1$ is preferably 3-oxabutyl, 3-oxapentyl, 3-oxahexyl, 3-oxaheotyl, 4-oxapentyl, 4-oxahexyl, 4-oxaheptyl or 4-oxaoctyl; $X_2$ and $X_3$ are preferably methyl, ethyl, propyl or isopropyl; $X_3$ is preferably methoxyl, ethoxyl or straight or branched propoxyl. Z is preferably methyl, ethyl, propyl, isopropyl or branched or straight chain butyl, pentyl or hexyl; and $R_1$ and $R_2$ are preferably methyl, ethyl, propyl or isopropyl.

Among the preferred compounds of formula I are those of the formula

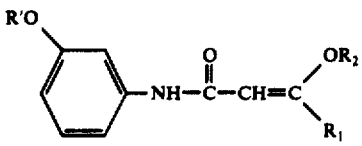

wherein $R_1$ and $R_2$ have the above definition and R' is

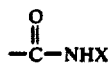

or

wherein X and Z have the above definitions. Most preferred are the compounds of formula I where $R_1$ and $R_2$ are methyl and R' is preferably

The novel process of the invention for the preparation of compounds of formula I comprises reacting a m-hydroxyacetylacetanilide of the formula

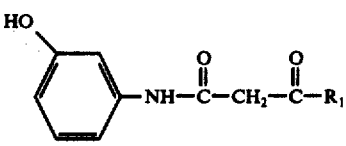

wherein $R_1$ has the above definition with an isocyanate of the formula $$X-N=C=O$$

or with acid chloride of the formula

to obtain a compound of the formula

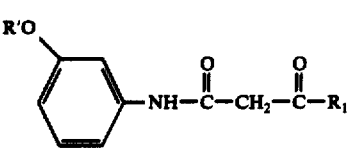

wherein R' and $R_1$ have the above definition and reacting the latter with an alkyl orthoformate of the formula $$H-C-(OR_2)_3$$

wherein $R_2$ has the above definition in the presence of an acid agent to obtain a compound of the formula

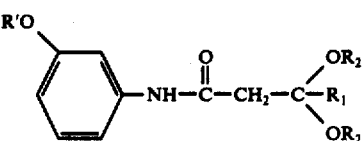

and heating the latter to form the corresponding compound of formula I

The reaction with the compound of formula II is effected in the presence of a small amount of the tertiary base such as pyridine or triethylamine and in an organic solvent such as benzene, toluene, tetrahydrofuran, ether, isopropyl ether or acetone. The acid agent present in the reaction with the alkyl orthoformate is preferably sulfuric acid or p-toluene sulfonic acid.

The process for the preparation of compounds of formula I' wherein R is

and X is alkoxyalkyl of 2 to 12 carbon atoms comprises reacting a m-hydroxyanilide of the formula

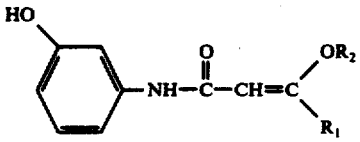

wherein $R_1$ and $R_2$ are alkyl of 1 to 3 carbon atoms with an isocyanate of the formula $X_1$-N=C=O wherein $X_1$ has the above definition. The reaction is preferably effected in an organic solvent such as ether or tetrahydrofuran and is preferably effected in the presence of a tertiary base such as pyridine and triethylamine.

The process of the invention for the preparation of the compounds of formula I' when R is

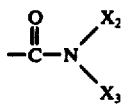

comprises reacting a m-hydroxy-acetylacetanilide of formula II with a cabamoyl chloride of the formula

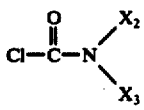

to obtain an acetanilide of the formula

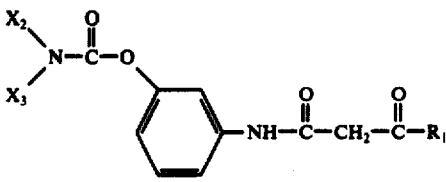

reacting the latter with an alkyl orthoformate of the formula H—C—(OR$_2$)$_3$ in the presence of an acid agent to obtain a compound of the formula

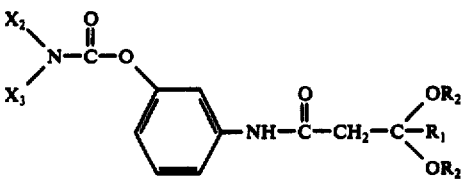

and heating the latter to obtain the corresponding compound of formula I'.

The reaction with the carbamoyl chloride is preferably effected in the presence of a basic agent. When $X_2$ and $X_3$ are both alkyl, a strong base such as sodium hydride is preferred and when one of $X_2$ and $X_3$ is alkoxy, a tertiary base such as pyridine or triethylamine is preferred. The acid agent is preferably p-toluene sulfonic acid or sulfuric acid.

The compounds of formula I' may be present in the form of their E isomers or their Z isomers mixtures thereof. The processes of the invention produce predominantly the E isomer.

For the starting materials for the process, m-hydroxyacetylacetanilide is described in German Pat. No. 571,319 and is prepared by reaction of m-aminophenol and ethyl acetylacetate. Other compounds of formula II may be made in an analogous fashion with other esters.

m-hydroxy-3-methoxy-crotonanilide of formula V may be prepared by reacting diketene with m-benzyloxy-aniline to form m-benzyloxy-acetylacetanilide which is then reacted with methyl orthoformate to form m-benzyloxy-3,3-dimethoxybutyranilide which is converted by hydrogenolysis into m-hydroxy 3,3-dimethoxy-butyranilide which is then heated. Other compounds of formula V may be made in an analogous fashion.

The novel herbicidal compositions are comprised of a herbicidally effective amount of at least one compound of formula I' and a carrier. The compositions are active against a wide variety of botanical families and will selectively destroy weeds without attacking grass crops such as cereals.

The compositions may contain also one or more other pesticidal agents or one or more other products which influence plant growth. The compositions usually contain 10 to 80 % by weight, preferably 10 to 50 % by weight, of the compounds of formula I'.

The compositions may be in he form of powders, granules, suspensions, emulsions or solutions containing besides compounds of formula I', cationic, anionic or non-ionic surface active agents, inert powders such as talc, clays, silicates or kieslguhr, or a vehicle such as water, alcohol, hydrocarbons, other organic solvents or a mineral, vegetable or animal oil.

The novel process of the invention for killing weeds comprises contacting the weeds with a herbicidally effective amount of at least one compound of formula I'. The preferred compounds are those of formula I and when R' is

$R_1$ and $R_2$ are preferably methyl. The compounds may be applied either pre- or post-emergence at a rate of 5 to 0.312 kg/ha.

In the following examples there are described several preferred embodiments to illustrate the invention. However, it should be understood that the invention is not intended to be limited to the specific embodiments.

EXAMPLE 1 m-(n-butylcarbamoyloxy)-3-methoxy-2-hexenanilide

STEP A: m-hydroxybutyrylacetanilide

A few drops of pyridine were added to a solution of 87 g of m-aminophenol in 600 ml of xylene and after heating the resulting mixture to 140° C, a solution of 126 g of ethyl butyrylacetate in 100 ml of xylene containing a few drops of pyridine was added thereto over 2 ½ hours. The mixture was held at 140° C for 2 hours and was then cooled. The mixture was vacuum filtered and the crystals were washed with xylene and then isopropyl ether to obtain 123 g of m-hydroxybutyrylacetanilide metlting at 228°–232° C.

STEP B: m-(n-butylcarbamoyloxy)-butyrylacetanilide 2 ml of triethylamine and then 28 g of n-butyl isocyanate were added to a solution of 43 g of m-hydroxybutyrylacetanilide in 500 ml of tetrahydrofuran and the mixture was refluxed for 1 ½ hours. The mixture was then stirred at room temperature for 20 hours and was then filtered. The filtrate was concentrated to dryness to obtain 56 g of m-(n-butylcarbamoyloxy)-butyrylacetanilide melting at 123° C.

STEP C: m-(n-butylcarbamoyloxy)-3,3-dimethoxy-hexananilide 41 g of methyl orthoformate and 1 g of p-toluene sulfonic acid were added to a solution of 54 g of the product of Step B in 170 ml of methanol and the mixture was stirred at room temperature for 20 hours. 1.5 ml of quinoline were added thereto and the solvent was evaporated. The residue was chromatographed over silica gel and was eluted with an 8–2 methylene chloride-acetone mixture to obtain 30 g of m-(n-butylcarbamoyloxy)-3,3-dimethoxy-hexanailide melting at 83° C.

STEP D: m-(n-butylcarbamoyloxy)-3-methoxy-2-hexenanilide

A mixture of 25 g of the product of Step C and 250 ml of toluene was heated at 140°C for 2 hours while removing the methanol formed and after cooling, the mixture was vacuum filtered. The recovered crystals were empasted with isopropyl ether and recrystallized from ethyl acetate to obtain 20 g of m-(n-butylcarbamoyloxy)-3-methoxy-2-hexenanilide (isomer E) melting at 150°C.

Analysis: $C_{18}H_{26}N_2O_4$.
Calculated: %C 64.65, %H 7.83, %N 8.37.
Found: %C 64.7, %H 8.1, %N 8.3.

EXAMPLE 2 m-(n-butylcarbamoyloxy)-3-ethoxy-crotonanilide

STEP A: m-(n-butylcarbamoyloxy)-acetylacetanilide

A mixture of 22 g of n-butyl isocyanate, 40 g of m-hydroxyacetylacetanilide, 140 ml of tetrahydrofuran and 1 ml of triethylamine was refluxed for an hour and then was cooled and vacuum filtered to obtain 40 g of m-(n-butylcarbamoyloxy)-acetylacetanilide melting at 112°C.

STEP B: m-(n-butylcarbamoyloxy)-3,3-diethoxy-butyranilide 52 g of ethyl orthoformate and 1 g of p-toluene sulfonic acid were added to a solution of 59 g of the product of Step A in 180 ml of methanol and the mixture was stirred at room temperature for 7 hours. The mixture was then allowed to stand for 18 hours and 1 ml of quinoline was added thereto. The solvent was evaporated and the residue was chromatographed over silica gel. Elution with an 8–2 methylene chloride-acetone mixture gave 20 g of m-(n-butylcarbamoyloxy)-3,3-diethoxy-butyranilide melting at 130°C.

Step C: m-(n-butylcarbamoyloxy)-3-ethoxy-crotonanilide

A mixture of 20 g of the product of Step B and 200 ml of toluene was heated at 140°C for 2 hours while removing the ethanol formed and after cooling, the mixture was vacuum filtered. The crystals were empasted with isopropyl ether and crystallized from ethyl acetate to obtain 11 g of m-(n-butylcarbamoyloxy)-3-ethoxy-crotonanilide (isomer E) melting at 164°C.

Analysis: $C_{17}H_{24}N_2O_4$.
Calculated: %C 63.73, %H 7.55, %N 8.74.
Found: %C 63.8, %H 7.8, %N 8.8.

EXAMPLE 3 m-(n-butylcarbamoyloxy)-3-methoxy-crotonanilide

STEP A: m-(n-butylcarbamoyloxy)-3,3-dimethoxy-butyranilide

A mixture of 23.5 g of m-(n-butylcarbamoyloxy)-acetylacetanilide 15 g of methyl orthoformate, 75 ml of methanol and 0.5 g of p-toluene sulfonic acid was stirred for 24 hours and 1 ml of quinoline was then added. The solvent was evaporated and the residue was chromatographed over silica. Elution with an 8-2 methylene chloride-acetone mixture yielded 20 g of m-(n-butylcarbamoyloxy)-3,3-dimethoxy-butyranilide melting at 114°C.

STEP B: m-(n-butylcarbamoyloxy)-3-methoxy-crotonanilide

A mixture of 43 g of m-(n-butylcarbamoyloxy)-3,3-dimethoxy-butyranilide and 400 ml of toluene were stirred at 140°C for 2 hours while removing the methanol formed and was then cooled and vacuum filtered to obtain 33 g of m-(n-butylcarbamoyloxy)-3-methoxy-crotonanilide (isomer E) melting at 166°C.

Analysis: $C_{16}H_{22}N_2O_4$.
Calculated: %C 62.71, %H 7.24, %N 9.14.
Found: %C 62.5, %H 7.5, %N 9.0.

EXAMPLE 4

Using the procedure of Example 1, m-hydroxyacetylacetanilide and methyl isocyanate were reacted to obtain m-methylcarbamoyloxy-acetylacetanilide melting at 142°C which was then reacted with methyl orthoformate to obtain m-methylcarbamoyloxy-3,3-dimethoxy-butyranilide melting at 139°C. The latter was heated to obtain m-methylcarbamoyloxy-3-methoxycrotonanilide melting at 175°C.

Analysis: $C_{13}H_{16}N_2O_4$.
Calculated: %C 59.07, %H 6.10, %N 10.60.
Found: %C 59.0, %H 5.9, %N 10.2.

EXAMPLE 5

Using the procedure of Example 1, m-hydroxyacetylacetanilide and ethyl isocyanate were reacted to form m-ethylcarbamoyloxy-acetylacetanilide melting at 138°C which was reacted with methyl orthoformate to obtain m-ethylcarbamoyloxy-3,3-dimethyoxy-butyranilide melting at 127°C. The latter product was heated to obtain m-ethylcarbamoyloxy-3-methoxycrotonanilide melting at 183°C.

Analysis: $C_{14}H_{18}N_2O_4$.
Calculated: %C 60.42, %H 6.52, %N 10.07.
Found: %C 60.4, %H 6.5, %N 10.1,

EXAMPLE 6

Using the procedure of Example 1, m-hydroxyacetylacetanilide and isopropyl isocyanate were reacted to obtain m-isopropylcarbamoyloxy-acetylacetanilide melting at 161°C which was then reacted with methyl orthoformate to obtain m-isopropylcarbamoyloxy-3,3-dimethoxy-butyranilide melting at 160°C. The latter product was heated to obtain m-isopropylcarbamoyloxy -3-methoxy-crotonanilide melting at 210°C.

Analysis: $C_{15}H_{20}N_2O_4$.

Calculated: %C 61.63, %H 6.89, %N 9.58.
Found: %C 61.5, %H 7.0, %N 9.5.

EXAMPLE 7

Using the procedure of Example 1, m-hydroxyacetylacetanilide and n-hexyl isocyanate were reacted to obtain m-(n-hexylcarbamoyloxy)-acetylacetanilide melting at 125°C which was then reacted with methyl orthoformate to obtain m-(n-hexylcarbamoyloxy)-3,3-dimethoxy-butyranilide melting at 110°C. The latter product was heated to obtain m-(n-hexylcarbamoyloxy)-3-methoxy-crotonanilide with a melting part of 146°C.

Analysis: $C_{18}H_{26}N_2O_4$.
Calculated: %C 64.64, %H 7.83, %N 8.38.
Found: %C 64.9, %H 7.9, %N 8.2.

EXAMPLE 8

Using the procedure of Example 1, m-hydroxyacetylacetanilide and cyclohexyl isocyanate were reacted to obtain m-cyclohexylcarbamoyloxy-acetylacetanilide melting at 159°C which was then reacted with methyl orthoformate to obtain m-cyclohexylcarbamoyloxy-3,3-dimethoxy-butyranilide melting at 163°C. The latter product was heated to obtain m-cyclohexylcarbamoyloxy-3-methoxy-crotonanilide melting at 200°C.

Analysis: $C_{18}H_{24}N_2O_4$.
Calculated: %C 65.04, %H 7.28, %N 8.43.
Found: %C 65.0, %H 7.3, %N 8.5.

EXAMPLE 9 m-valeryloxy-3-methoxy-crotonanilide

STEP A: m-valeryloxy-acetylacetanilide 48 g of valeryl chloride were added over 30 minutes to a mixture of 70 g of m-hydroxyacetanilide, 500 ml of tetrahydrofuran and 40 g of triethylamine and after stirring the mixture for 4 hours at room temperature, the mixture was allowed to stand for 20 hours. The mixture was filtered and the filtrated was evaporated to dryness. The residue was chromatographed over silica gel and was eluted with an 8-2 methylene chloride-acetone mixture to obtain 47 g of m-valeryloxy-acetylacetanilide melting at 65°C.

STEP B: m-valeryloxy-3-methoxy-crotonanilide

A solution of 47 g of m-valeryloxy-acetylacetanilide in 50 ml of methyl orthoformate and 0.5 g of p-toluene sulfonic acid stood at room temperature for 16 hours and then 1 g of quinoline and 200 ml of toluene were added thereto. The mixture was heated at 140°C for 4 hours while removing the methanol formed and the solvent was then evaporated. The residue was chromatographed over silica gel and was eluted with an 8-2 methylene chloride-acetone mixture to obtain 25 g of m-valeryloxy-3-methoxy-crotonanilide (isomer E) melting at 84°C.

Analysis: $C_{16}H_{21}NO_4$.
Calculated: %C 65.96, %H 7.27, %N 4.80.
Found: %C 66.1, %H 7.2, %N 4.8.

EXAMPLE 10 m-(β-ethoxyethylcarbamoyloxy-3-methoxy-crotonanilide

STEP A: m-benzyloxy-acetylacetanilide 84 g of diketene were added over 30 minutes to a mixture of 200 g of m-benzyloxy-aniline [Morton, J. Biol. Chem., (1949), p. 259] in 1 liter of benzene cooled to 10°C and after stirring the mixture for 6 hours, the benzene was distilled off under reduced pressure. The residue was added to isopropyl ether and the mixture was vacuum filtered. The recovered precipitate was washed with isopropyl ether and dried to obtain 240 g of m-benzyloxy-acetylacetanilide melting at 80°C.

STEP B: m-benzyloxy-3,3-dimethoxy-butyranilide

A mixture of 70 g of m-benzyloxy-acetylacetanilide, 37 g of methyl orthoformate and 100 ml of methanol was stirred at 20°C for 16 hours and 2 ml of quinoline were added thereto. The mixture was concentrated to dryness under reduced pressure and the residue was added to isopropyl ether. The mixture was cooled and vacuum filtered and the recovered precipitate was dried and chromatographed over silica gel. Elution with an 8-2 methylene chloride-acetone mixture gave 48 g of m-benzyloxy-3,3-dimethoxy-butyranilide melting at 83°C.

STEP C: m-hydroxy-3,3-dimethoxy-butyranilide 2 g of palladized activated carbon titrating 8% of palladium hydroxide were added to a solution of 33 g of m-benzyloxy-3,3-dimethoxy-butyranilide in 500 ml of ethanol and the mixture was stirred with hydrogen at 20°C. After 8 hours during which the theoretical amount of hydrogen was consumed, the mixture was filtered and the filtrate was concentrated to dryness under reduced pressure. The precipitate was added to isopropyl ether and the mixture was vacuum filtered. The precipitate was washed and dried to obtain 22 g of m-hydroxy-3,3-dimethoxy-butyranilide melting at 136°C.

STEP D: m-hydroxy-3-methoxy-crotonanilide

A mixture of 37 g of m-hydroxy-3,3-dimethoxy-butyranilide and 200 ml of toluene was heated at 145°C with stirring for 4 hours while distilling a benzene-methanol azeotrope and was then cooled. The mixture was vacuum filtered and the recovered crystals were dried to obtain 24 g of m-hydroxy-3-methoxy-crotonanilide melting at 166°C.

Analysis: $C_{11}H_{13}NO_3$.
Calculated: %C, 63.76, %H 6.32, %N 6.76.
Found: %C 63.9, %H 6.3, %N 6.6.

STEP E: m-(β-ethoxyethylcarbamoyloxy)-3-methoxy-crotonanilide

A mixture of 2 ml of triethylamine, 31 g of m-hydroxy-3-methoxy-crotonanilide, 20 g of β-ethoxyethyl isocyanate [Ulrich et al, J. Org., Vol. 31 (1966), p. 2658] and 350 ml of tetrahydrofuran was refluxed for 3 hours and then concentrated under reduced pressure. After standing for 50 hours at 20°C, isopropyl ether was added thereto and the mixture was vacuum filtered. The recovered precipitate was dried and chromatographed over silica gel. The product was eluted with an 8-2 methylene chloride-acetone mixture and was then suspended in 100 ml of 0.1N sodium hydroxide solution. The mixture was vacuum filtered and the precipitate was washed with water and dried to obtain 21 g of m-(β-ethoxyethylcarbamoyloxy)-3-methoxy-crotonanilide melting at 133°-134°C.

Analysis: $C_{16}H_{22}N_2O_5$.
Calculated: %C 59.62, %H 6.88, %N 8.69.
Found: %C 59.6, %H 7.0, %N 8.4.

EXAMPLE 11 m-(N-dimethylcarbamoyloxy)-3-methoxy-crotonanilide

STEP A: m-(N-dimethylcarbamoyloxy)-acetylacetanilide 4.8 g of a 50% suspension of sodium hydride in mineral oil was added portion wise to a mixture of 19.3 g of m-hydroxyacetylacetanilide and 200 ml of tetrahydrofuran and the mixture was stirred for one hour after which hydrogen evolution ceased. 10.75 g of dimethycarbamoyl chloride were added to the reaction mixture which was then stirred for 24 hours and was filtered. The filtrate was evaporated to dryness and the residue was added to chloroform. Filtration of the mixture removed 2 g of m-hydroxy-acetylacetanilide and the filtrate was treated with activated carbon, filtered and evaporated to dryness to obtain 28.5 g of m-(N-dimethylcarbamoyloxy)-acetylacetanilide which was used as is for the next step.

STEP B: m-(N-dimethylcarbamoyloxy)-3-methoxy-crotonanilide

A mixture of 28.5 g of m-(N-dimethylcarbamoyloxy)-acetylacetanilide, 0.4 g of p-toluene sulfonic acid, 28.5 g of methyl orthoformate and 60 ml of methanol was stirred for 24 hours at room temperature and after the addition of 0.4 g of quinoline, the mixture was concentrated to dryness to obtain 26 g of raw m-(N-dimethylcarbamoyloxy)-3,3-dimethoxybutyranilide. The product was dissolved in 170 ml of toluene and heated for 6 hours at 140°C while distilling a methanoltoluene azeotrope and was then concentrated to dryness. The residue was chromatographed over silica gel and was eluted with an 8-2 methylene chloride-acetone mixture. The product was crystallized from ethyl acetate to obtain 24.5 g of m-(N-dimethylcarbamoyloxy)-3-methoxy-crotonanilide melting at 150°C.

Analysis: $C_{14}H_{18}N_2O_4$.
Calculated: %C 60.42, %H 6.52, %N 10.07, %0.23.
Found: %C 60.3, %H 6.4, %N 9.7, % 22.9.

EXAMPLE 12 m-(N-methyl-N-methoxy-carbamoyloxy)-3-methoxy-crotonanilide

STEP A: m-(N-methyl-N-methoxycarbamoyloxy)-acetylanilide

A mixture of 19.3 g of m-hydroxy-acetylacetanilide, 10 g of triethylamine, 12.35 g of methylmethoxy-carbamoyl chloride and 200 ml of tetrahydrofuran was stirred for 1 hour at 20°C and was then refluxed for 24 hours and then filtered. The filtrate was evaporated to dryness and the residue was added to chloroform. The mixture was filtered to remove 1 g of m-hydroxy-acetylacetanilide and the filtrate was evaporated to dryness to obtain 32.5 g of m-(N-methyl-N-methoxycarbamoyloxy)-acetylacetanilide which was used as is for the next step.

STEP B: m-(N-methyl-N-methoxy-carbamoyloxy)-3-methoxycrotonanilide

A mixture of 32.5 g of m-(N-methyl-N-methoxy-carbamoyloxy)-acetylacetanilide, 0.4 g of p-toluene sulfonic acid, 32.5 g of methyl orthoformate and 60 ml of methanol was stirred for 24 hours at 20°C and after the addition of 0.4 g of quinoline, the mixture was evaporated to dryness to obtain 40 g of m-(N-methyl-N-methoxy-carbamoyloxy)-3,3-dimethoxy-butyranilide. The product was dissolved in 175 ml of toluene and the solution was heated at 140°C for 5 hours while distilling off a toluene-methanol azeotrope. The mixture was then evaporated to dryness and the residue was chromatographed over silica gel. Elution with a 9-1 methylene chloride-acetone mixture yielded 11.5 g of m-(N-methoxy-carbamoyloxy)-3-methoxy-crotonanilide with a refractive index $n_D^{20} = 1.544$.

Analysis: $C_{14}H_{18}N_2O_5$.
Calculated: %C 57.15, %H 6.16, %N 0.52.
Found: %C 57, %H 6.3, %N 9.

EXAMPLE 13 m-acetoxy-3-methoxy-crotonanilide

Using the procedure of Example 1, m-hydroxy-acetylacetanilide and acetyl chloride were reacted to obtain m-acetoxy-acetylacetanilide melting at 101°C. Acetic acid anhydride could also be used.

A mixture of 50 g of m-acetoxy-acetylacetanilide, 1 g of p-toluene sulfonic acid and 50 ml of methyl orthoformate was stirred for 16 hours at 20°C and after the addition of 2 ml of quinoline and 200 ml of toluene, the reaction mixture was heated at 140°C for 4 hours while distilling off a toluene-methanol azeotrope. The mixture was evaporated to dryness under reduced pressure and the residue was chromatographed over silica gel. The product was eluted with an 8-2 methylene chloride-acetone mixture and was crystallized from isopropyl ether to obtain 29.5 g of m-acetoxy-3-methoxy-crotonanilide melting at 111°C.

Analysis: $C_{13}H_{15}NO_4$.
Calculated: %C 62.65, %H 6.06, %N 5.62.
Found: %C 63.1, %H 6.2, %N 5.3.

EXAMPLE 14

A wettable herbicidal powder was prepared from 25% by weight of m-methylcarbamoyloxy-3-methoxy-crotonanilide, 15% by weight of Ekapersol S (condensation product of sodium naphthalene sulfonate), 0.5% by weight of Brecolane NVA (sodium alkyl naphthalene sulfonate), 34.5% by weight of Zeosil 39 (precipitated synthetic hydrated silica) and 25% by weight of Vercoryl S (colloided silica).

EXAMPLE 15

A wettable powder was prepared comprising 25% by weight of m-(β-ethoxyethylcarbamoyloxy)-3-methoxy-crotonanilide, 10% by weight of Ekapersol S, 0.5% by weight of Brecolane NVA, 34.5% by weight of Zeosil 39 and 30% by weight of Vercoryl S. To obtain a sprayable mixture, the said powder could be mixed with desired amount of water to obtain the amount of active ingredient wanted.

EXAMPLE 16

An emulsified concentrate in the form of a concentrated homogenous liquid was prepared from 25% by weight of m-(N-dimethylcarbamoyloxy)-3-methoxy-crotonanilide, 6.4% by weight of Atlox4851 (mixture of alkylarylsulfonate and polyoxyethylene triglyceride with a viscosity of 300–700 cps at 25°C), 3.2% by weight of Atlox 4855 (mixture of alkylarylsulfonate and polyoxyethylene triglyceride with a viscosity of 1500–1900 cps at 25°C) and 64.4% by weight of xylene. To obtain a sprayable composition, the said concentrate is mixed with a sufficient amount of water to obtain the desired concentrated of active ingredient.

PRE-AND POST-EMERGENCE HERBICIDAL ACTIVITY

A. m-methylcarbamoyloxy-3-methoxy-crotonanilide (compound A), m-(n-butylcarbamoyloxy)-3-methoxy-crotonanilide (compound B) and m-(isopropylcarbamoyloxy)-3-methoxy-crotonanilide (compound C) were tested on plant species planted in a culture box (23 × 14 × 4 cm) with a double bottom and with watering from underneath. 20 seeds for each species were planted in rows 3 cm apart in a single box and 4 tests were run for each concentration. The plants were held at 60% relative humidity at 20°C ± 2°C with lighting by fluorescent tubes (daylight and white light) from 6 to 22 hours each day. The dirt mixture was 10 volumes of pure dirt, 2 volumes of peat and 10 volumes of river sand.

In the pre-emergence test, treatment was effected 24 hours after the sowing and the first watering was effected by aspersion so that a part of the product was carried to the level of the seeds. In the post-emergence test, treatment was effected on the above ground portion after 21 days of culture.

In both cases, the test products were applied under standard conditions with a microsprayer at doses of 5, 2.5, 1.25 and 0.625 Kg/ha at a dilution equal to 560 1/ha. The final readings was determined by the weight of the plants 21 days after the pre-emergence treatment and 15 days after the post-emergence treatment. The results in Tables I to III are expressed as a percent of reduction of the vegetation P calculated as follows:

$$P = \frac{\text{weight of control plants} - \text{weight of treated plants}}{\text{weight of control plants}} \times 100$$

B. The herbicidal activity of m-(N-dimethylcarbamoyloxy) 3-methoxy-crotonailide (compound D) and m-(β-ethoxyethylcarbamoyloxy)-3-methoxy-crotonanilide (compound E) was tested as in the preceding test except that the number of plants was counted after 21 days after treatment in the pre-emergence test and 15 days after treatment in the post-emergence test. The results were expressed as percent of mortality M as follows:

$$M = \frac{\text{No. of control plants} - \text{No. of treated plants still living}}{\text{No. of control plants}} \times 100$$

TABLE IV

| | POST-EMERGENCE COMPOUND D | | | |
|---|---|---|---|---|
| Tested | Doses in Kg/ha | | | |
| plants | 5 | 2.5 | 1.25 | 0.625 |
| Triticum Sativum | 100 | 58 | 0 | 0 |
| Hordeum Spec | 90 | 0 | 0 | 0 |
| Zea Mays | 0 | 0 | 0 | 0 |
| Avena Sativa | 100 | 50 | 0 | 0 |
| Agrostis Tenuis | 100 | 100 | 100 | 90 |
| Lolium Perenne | 100 | 0 | 0 | 0 |
| Alopecurus Myosuroides | 100 | 100 | 0 | 0 |
| Beta Vulgaris | 100 | 100 | 100 | 100 |
| Chenopodium Quinoa | 100 | 100 | 100 | 100 |
| Chrysanthemum Coronarium | 100 | 100 | 100 | 100 |
| Galium Aparine | 100 | 100 | 100 | 50 |
| Sinapis Alba | 100 | 100 | 100 | 100 |
| Rumex Crispus | 100 | 100 | 100 | 100 |
| Trifolium Praetense | 100 | 100 | 100 | 100 |

TABLE I

| | COMPOUND A — POST-EMERGENCE | | | | | | | | | | | | | |
|---|---|---|---|---|---|---|---|---|---|---|---|---|---|---|
| Doses in Kg/ha | A | B | C | D | E | F | G | H | I | J | K | L | M | N |
| 5 | 100 | 100 | 100 | 15 | 100 | 80 | 80 | 100 | 100 | 100 | 100 | 100 | 100 | 100 |
| 2.5 | 0 | 34 | 0 | 0 | 90 | 0 | 0 | 100 | 100 | 100 | 100 | 100 | 100 | 100 |
| 1.25 | 0 | 0 | 0 | 0 | 65 | 0 | 0 | 100 | 100 | 100 | 84 | 100 | 100 | 86 |
| 0.625 | 0 | 0 | 0 | 0 | 0 | 0 | 0 | 100 | 74 | 100 | 68 | 100 | 53 | 25 |
| 0.312 | | | | | | | | 95 | 100 | 72 | 0 | 94 | 0 | 21 |
| 0.156 | | | | | | | | 77 | 85 | 35 | 0 | 41 | 0 | 0 |

TABLE II

| | COMPOUND B — PRE-EMERGENCE | | | | | | | | | | | | | |
|---|---|---|---|---|---|---|---|---|---|---|---|---|---|---|
| Doses in Kg/ha | A | B | C | D | E | F | G | H | I | J | K | L | M | N |
| 5 | 90 | 32 | 59 | 0 | 100 | 100 | 73 | 100 | 100 | 100 | 26 | 100 | 100 | 100 |
| 2.5 | 48 | 0 | 0 | 0 | 100 | 100 | 44 | 100 | 100 | 100 | 40 | 100 | 100 | 100 |
| 1.25 | 0 | 0 | 0 | 0 | 97 | 42 | 0 | 100 | 100 | 100 | 37 | 100 | 100 | 100 |
| 0.625 | 0 | 0 | 0 | 0 | 59 | 0 | 0 | 61 | 0 | 88 | 0 | 84 | 0 | 88 |

TABLE III

| | COMPOUND C — PRE-EMERGENCE | | | | | | | | | | | | | |
|---|---|---|---|---|---|---|---|---|---|---|---|---|---|---|
| Doses in Kg/ha | A | B | C | D | E | F | G | H | I | J | K | L | M | N |
| 5 | 100 | 68 | 71 | 29 | 100 | 100 | 100 | 100 | 100 | 100 | 58 | 100 | 100 | 100 |
| 2.5 | 82 | 24 | 71 | 0 | 100 | 100 | 100 | 100 | 100 | 100 | 64 | 100 | 100 | 100 |
| 1.25 | 30 | 0 | 0 | 0 | 100 | 87 | 58 | 100 | 100 | 100 | 56 | 100 | 100 | 100 |
| 0.625 | 0 | 0 | 0 | 0 | 90 | 55 | 38 | 88 | 96 | 90 | 68 | 85 | 72 | 100 |

A : Oats
B : Wheat
C : Barley
D : Corn
E : Bent Grass
F : Rye Grass
G : Alopecurus
H : Beets
I : Chenopode
J : Chrysanthum
K : Gaillet
L : Mustard
M : Rumex
N : Clover

TABLE V

| POST-EMERGENCE COMPOUND E | | | | |
|---|---|---|---|---|
| Tested | Doses in Kg/ha | | | |
| plants | 5 | 2.5 | 1.25 | 0.625 |
| Triticum Sativum | 0 | 0 | 0 | 0 |
| Hordeum Spec | 33 | 0 | 0 | 0 |
| Zea Mays | 0 | 0 | 0 | 0 |
| Avena Sativa | 32 | 0 | 0 | 0 |
| Agrostis Tenuis | 100 | 93 | 91 | 37 |
| Lolium Perenne | 82 | 0 | 0 | 0 |
| Alopecurus Myosuroides | 44 | 41 | 39 | 24 |
| Beta Vulgaris | 100 | 71 | 43 | 68 |
| Chenopodium Quinoa | 82 | 57 | 59 | 79 |
| Chrysanthemum Coronarium | 100 | 100 | 100 | 96 |
| Galium Aparine | 70 | 73 | 24 | 0 |
| Sinapis Alba | 100 | 100 | 100 | 82 |
| Rumex Crispus | 95 | 88 | 84 | 51 |
| Trifolium Praetense | 100 | 100 | 100 | 88 |

TABLE VI

| PRE-EMERGENCE COMPOUND E | | | | |
|---|---|---|---|---|
| Tested | Doses in Kg/ha | | | |
| plants | 5 | 2.5 | 1.25 | 0.625 |
| Triticum Sativum | 0 | 0 | 0 | 0 |
| Hordeum Spec | 33 | 0 | 0 | 0 |
| Zea Mays | 0 | 0 | 0 | 0 |
| Avena Sativa | 32 | 0 | 0 | 0 |
| Agrostis Tenuis | 100 | 93 | 91 | 37 |
| Lolium Perenne | 82 | 0 | 0 | 0 |
| Alopecurus Myosuroides | 44 | 41 | 39 | 24 |
| Beta Vulgaris | 100 | 71 | 43 | 68 |
| Chenopodium Quinoa | 82 | 57 | 59 | 79 |
| Chrysanthemum Coronarium | 100 | 100 | 100 | 96 |
| Galium Aparine | 70 | 73 | 24 | 0 |
| Sinapis Alba | 100 | 100 | 100 | 82 |
| Rumex Crispus | 95 | 88 | 84 | 51 |
| Trifolium Praetense | 100 | 100 | 100 | 80 |

It can be concluded from the foregoing Tables that the compounds of formula I' possess a good herbicidal activity against a number of dicotyledons and certain grasses without harm to cultivated grasses.

Various modifications of the products and methods of the invention may be made without departing from the spirit or scope thereof and it should be understood that the invention is intended to be limited only as defined in the appended claims.

We claim:

1. A compound of the formula

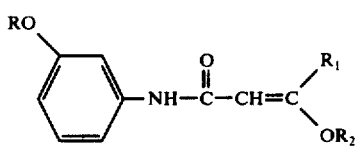

wherein R is selected from the group consisting of

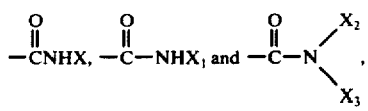

X is selected from the group consisting of alkyl of 1 to 8 carbon atoms and cycloalkyl of 3 to 7 carbon atoms, $X_1$ is alkoxyalkyl of 2 to 12 carbon atoms, $X_2$ is alkyl of 1 to 3 carbon atoms, $X_3$ is selected from the group consisting of alkyl of alkoxy of 1 to 3 carbon atoms, and $R_1$ and $R_2$ are individually alkyl of 1 to 3 carbon atoms.

2. A compound of claim 1 wherein R is

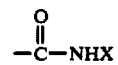

3. A compound of claim 1 wherein R is

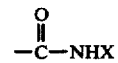

and X is alkyl of 1 to 8 carbon atoms.

4. A compound of claim 3 wherein $R_1$ and $R_2$ are methyl.

5. A compound of claim which is m-(n-butylcarbamoyloxy)-3-ethoxy-crotonanilide.

6. A compound of claim 1 which is m-(n-butylcarbamoyloxy)-3-methoxy-crotonanilide.

7. A compound of claim 1 which is m-(methoxycarbamoyloxy)-3-methoxy-crotonanilide.

8. A compound of claim 1 which is m-(ethylcarbamoyloxy)-3-methoxy-crotonanilide.

9. A compound of claim 1 which is m-(isopropylcarbamoyloxy)-3-methoxy-crotonanilide.

10. A compound of claim 1 which is m-(n-hexylcarbamoyloxy)-3-methoxy-crotonanilide.

11. A compound of claim 1 which is m-(cyclohexylcarbamoyloxy)-3-methoxy-crotonanilide.

12. A compound of claim 1 which is m-(β-ethoxyethylcarbamoyloxy)-3-methoxy-crotonanilide.

13. A compound of claim 1 which is m-(N-dimethylcarbamoyloxy)-3-methoxy-crotonanilide.

14. A compound of claim 1 which is m-(N-methyl-N-methoxy carbamoyloxy)-3-methoxy-crotonanilide.

15. A compound of claim 1 which is m-(n-butylcarbamoyloxy)-3-methoxy-2-hexenanilide.

16. A herbicidal composition comprising a herbicidally effective amount of at least one compound of claim 1 and a carrier.

17. A composition of claim 16 wherein R is

18. A method of killling weeds comprising contacting the weeds with a herbicidally effective amount of at least one compound of claim 1.

19. The method of claim 18 wherein R is

20. The method of claim 18 wherein R is

and X is alkyl of 1 to 8 carbon atoms.

21. The method of claim 20 wherein $R_1$ and $R_2$ are methyl.

22. The method of claim 18 wherein the compound is applied pre-emergence.

23. The method of clalim 18 wherein the compound is applied post-emergence.

* * * * *